US008845961B2

(12) United States Patent
Bernstein

(10) Patent No.: US 8,845,961 B2
(45) Date of Patent: *Sep. 30, 2014

(54) DEVICES AND ARTICLES COMPRISING UP-CONVERTING STERILIZING COMPOSITIONS AND METHODS FOR USING THE SAME

(71) Applicant: Phase Shield LLC, Dover, DE (US)

(72) Inventor: Eirc F. Bernstein, Gladwyne, PA (US)

(73) Assignee: Phase Shield LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/778,908

(22) Filed: Feb. 27, 2013

(65) Prior Publication Data

US 2013/0224071 A1 Aug. 29, 2013

Related U.S. Application Data

(60) Continuation of application No. 13/557,189, filed on Jul. 24, 2012, and a division of application No. 12/269,900, filed on Nov. 13, 2008, now Pat. No. 8,236,239.

(60) Provisional application No. 60/988,466, filed on Nov. 16, 2007.

(51) Int. Cl.
| | | |
|---|---|---|
| *A61L 2/00* | (2006.01) | |
| *A61N 5/00* | (2006.01) | |
| *C09K 11/08* | (2006.01) | |
| *A01N 59/26* | (2006.01) | |
| *C01B 25/00* | (2006.01) | |
| *C09K 11/77* | (2006.01) | |
| *A61L 2/08* | (2006.01) | |
| *A61L 2/10* | (2006.01) | |
| *C09K 11/66* | (2006.01) | |

(52) U.S. Cl.
CPC ............... *A61L 2/10* (2013.01); *C09K 11/7769* (2013.01); *A61L 2202/24* (2013.01); *C09K 11/7706* (2013.01); *A61L 2/081* (2013.01); *C09K 11/7774* (2013.01); *C09K 11/7789* (2013.01); *C09K 11/7705* (2013.01); *C09K 11/7777* (2013.01); *A61L 2/084* (2013.01); *A61L 2/085* (2013.01); *C09K 11/778* (2013.01); *C09K 11/663* (2013.01); *C09K 11/7701* (2013.01); *C09K 11/7771* (2013.01)

USPC .... 422/23; 250/492.1; 250/581; 252/301.4 P; 252/519.34; 424/601; 423/299

(58) Field of Classification Search
CPC ........... A61K 8/24; A01N 1/0294; C09D 5/22
USPC .............. 422/1, 23–24, 186, 186.3; 435/7.22, 435/7.32, 34; 250/492.1, 581; 252/301.4 P, 252/519.34; 424/601; 423/299
See application file for complete search history.

(56) References Cited

U.S. PATENT DOCUMENTS

| | | | |
|---|---|---|---|
| 5,698,397 A | 12/1997 | Zarling et al. | |
| 2005/0227864 A1* | 10/2005 | Sutorik et al. | ............... 502/304 |
| 2007/0241661 A1 | 10/2007 | Yin | |

FOREIGN PATENT DOCUMENTS

| | | | | |
|---|---|---|---|---|
| GB | 2013233 A | | 8/1979 | |
| JP | 09-067764 A | | 3/1997 | |
| JP | 2001 065034 A | | 3/2001 | |
| JP | 09-067764 | * | 11/2003 | ............ D06M 11/36 |
| WO | WO 9416623 A1 | | 8/1994 | |
| WO | WO 2007/082663 A1 | | 7/2007 | |

OTHER PUBLICATIONS

Japanese Patent Office English Translation of the Detailed Section of JP 09-067764.*
International Search Report mailed Jun. 17, 2009 in corresponding PCT Application No. PCT/US2008/083343.
International Preliminary Report on Patentability mailed May 27, 2010 in corresponding PCT Application No. PCT/US2008/083343.

* cited by examiner

*Primary Examiner* — Monzer R Chorbaji
(74) *Attorney, Agent, or Firm* — The Marbury Law Group, PLLC

(57) ABSTRACT

There is disclosed various devices and articles comprising phosphors for converting electromagnetic energy to radiation having a shorter wavelength, the composition comprising at least one phosphor capable of converting an initial electromagnetic radiation having a wavelength (A) to an electromagnetic radiation having a shorter wavelength (B) comprising UV radiation or radiation of a shorter wavelength. There is also a method of sterilizing such devices and articles by exposing it to UV radiation or radiation of a shorter wavelength for a time sufficient to deactivate or kill at least one microorganism and/or for a time sufficient to inhibit abnormal cell growth within the body, when the composition is in an implantable medical device.

35 Claims, No Drawings

DEVICES AND ARTICLES COMPRISING UP-CONVERTING STERILIZING COMPOSITIONS AND METHODS FOR USING THE SAME

This application is a continuation-in-part of U.S. patent application Ser. No. 13/557,189, filed Jul. 24, 2012, which is a divisional of U.S. application Ser. No. 12/269,900, filed Nov. 13, 2008, now U.S. Pat. No. 8,236,239, which claims the benefit of U.S. Provisional Application No. 60/988,466, filed Nov. 16, 2007, all three of which are incorporated herein by reference.

The present invention relates to a germicidal composition that can be formed into or used in various consumer, medical, and industrial products. The composition comprises organic or inorganic phosphors that convert an incident radiation to UVC radiation or electromagnetic radiation of shorter wavelengths, such as x-rays or gamma-rays for the purpose of sterilization by elimination, inactivation or reduction of pathogens including viruses, bacteria, fungi, yeast or prions. The present invention also relates to methods for making consumer, medical and industrial products from such compositions, as well as sterilizing such consumer products by applying an incident radiation that will be converted to UVC radiation or electromagnetic radiation of shorter wavelengths.

It is known that UV-C light is "germicidal" because it can deactivate the DNA of bacteria, viruses and other pathogens and thus destroys their ability to multiply and cause disease. In addition to such ultraviolet germicidal radiation, gamma rays and x-rays have been used to disinfect and purify water, air, and surfaces without the need for heat or chemicals. The short wavelength associated with UVC energy, specifically between about 250 to about 260 nm, and lower, provides the highest germicidal effectiveness, and thus is lethal to a variety or microorganisms, including the most common molds, virus, and bacteria, such as *salmonella, staphylococcus, streptococcus, legionella, bacillus*, dysentery, infectious hepatitis, influenza, and *rotavirus*.

The most common way to use UVC technology has long been germicidal lamps that emit a wavelength of energy of approximately 254 nm, since this is the region of maximum germicidal effectiveness. While UVC technology is both effective and free of unwanted by-products, it also has some inherent drawbacks, including the costs of the lamps and the dangers associated with direct or reflected germicidal radiation.

Accordingly, there is a need for a more economical and safer method of using the powerful germicidal effects of UV technology. To that end, the Inventor has investigated the use of organic or inorganic phosphors in a composition that will benefit from germicidal effects.

A phosphor is a substance that exhibits the phenomenon of phosphorescence, or a sustained glowing after exposure to light or energized particles such as electrons. Phosphors have a finite emission time, with persistence being inversely proportional to wavelength. Because the persistence of the phosphor increases as the wavelength decreases, it is known that red and orange phosphors do not have sufficiently long glow times.

The organic and inorganic phosphors used in the present invention differ from these traditional phosphors in that they have an indefinite glow time. In addition, they have the ability to transfer electromagnetic energy of one frequency to a higher frequency (referred to as "up-converting") or to a lower frequency (referred to as "down-converting"), depending on the rare earth metal used. A description of such phosphors is provided U.S. Pat. No. 5,698,397 (the '397 patent), and U.S. Pat. No. 4,857,228 (the '228 patent), both of which are herein incorporated by reference in their entireties. In particular, the '397 patent describes the use of such phosphors for biological and other assays. The '228 patent describes alkaline earth/chalcogen based phosphors, and methods of making the same.

Up-converting crystals, which take light or electromagnetic radiation of one frequency and convert it to light of a higher frequency (thus shorter wavelength), appear to contradict a basic law of physics directed to conservation of energy. However, two, four or more photons of a lower frequency or longer wavelength are converted into a single photon of higher frequency or shorter wavelength. Thus a number of photons of lower energy combine to produce one photon of higher energy. These compounds can emit visible light when irradiated with infra-red light.

In contrast, down-converting crystals take light or electromagnetic radiation of one frequency and convert it to light of a lower frequency (thus longer wavelength). These compounds can emit red or IR light when irradiated with UV or visible light.

The Inventor has surprisingly discovered that when incorporated into various media, such as resins, ceramics, and fabrics, the disclosed phosphors can change the frequency of visible or infrared light to germicidal UVC radiation, or electromagnetic radiation of shorter wavelengths, such as x-rays or gamma-rays for the purpose of sterilization by elimination, inactivation or reduction of pathogens including viruses, bacteria, fungi, yeast or prions. In addition, because the incident radiation is in the visible, infrared or longer wavelength ultraviolet region, there are no dangers associated with direct or reflected UV radiation. Rather, all the germicidal UV and shorter wavelength radiation impinges only on the article or area that contains the inventive composition. Because of these novel and other benefits, others have tried to duplicate the initial work. For example, published U.S. Patent Applications 2010/0297206 and 2011/0171062, both of which incorporated by reference in their entireties, describe antimicrobial articles, devices, coatings and the like, using various versions of Applicant's prior work.

SUMMARY OF INVENTION

Thus, the present disclosure is directed to a composition for converting electromagnetic energy to ultraviolet C (UVC) radiation or electromagnetic radiation of shorter wavelengths, such as x-rays or gamma-rays, for the purpose of sterilization by elimination, inactivation or reduction of pathogens including viruses, bacteria, fungi, yeast or prions. In one embodiment, the composition comprises, in an organic or inorganic media, at least one phosphor capable of converting an initial electromagnetic energy (A) to UVC radiation or electromagnetic radiation of shorter wavelengths than UVC such as x-rays or gamma-rays. The materials that can be used herein is based on the ternary rare earth metal orthophosphate, a crystalline solid composed of a host lattice of yttrium lutetium scandium orthophosphate that is activated with a small amount of dopants selected from bismuth, praseodymium and neodymium There is also disclosed a method of sterilizing an article by exposing it to UV-C radiation or electromagnetic radiation of shorter wavelengths such as x-rays or gamma-rays. In one embodiment, the method comprises exposing to visible, infrared or long wavelength UV radiation, a composition comprising, in an organic or inorganic media, at least one phosphor capable of converting the visible or infrared light to UVC radiation or radiation of a shorter wavelength, wherein the article is exposed for a time sufficient to deactivate or kill at least one microorganism chosen from bacteria, virus, mold, protozoa, and yeast.

There is also disclosed a method of inhibiting abnormal cell growth in a living body. In one embodiment, the method comprises exposing an article coated with the inventive composition, such as a stent, to visible or IR radiation (initial radiation A), so that it is converted to UVC radiation or electromagnetic radiation of shorter wavelengths such as x-rays or gamma-rays. The coated article can be exposed to the initial radiation (A) for a time sufficient to inhibit abnormal cell growth within the body, when the composition is in or on an implantable medical device.

There is also disclosed a method of coating an article with a sterilizing composition described herein. In this embodiment, the method comprises spraying, dipping, painting, or otherwise impregnating, on the article, a composition as described herein.

DETAILED DESCRIPTION OF THE INVENTION

Definitions

Certain terms used herein are defined below:

"Up-converting" refers to the ability to convert electromagnetic energy to a higher energy or shorter wavelength.

"Down-converting" refers to the ability to convert electromagnetic energy to a lower energy or longer wavelength.

"At least one" as used herein means one or more and thus includes individual components as well as mixtures/combinations.

A "film," as used herein, refers to a continuous coating, i.e., a coating without holes visible to the naked eye, which covers at least a portion of the substrate to which the composition was applied. Further, a film, as used herein, may have any thickness and is not restricted to a thin coating.

"Film-forming polymer" as used herein means a polymer which, by itself or in the presence of a film-forming auxiliary, is capable, after dissolution in at least one solvent, of forming a film on the substrate to which it is applied once the at least one solvent evaporates.

"Polymers" as defined herein comprise copolymers (including terpolymers) and homopolymers, including but not limited to, for example, block polymers, cross linked polymers, and graft polymers.

"Photosensitive agents" or "photosensitizers" as defined herein refers to a chemical compound that changes form or undergoes a reaction with another chemical compound upon exposure to electromagnetic radiation.

"Photodynamic therapy" as defined herein refers to a method of treating a condition by exposing a body part or a sample from a body to electromagnetic radiation.

"Blood irradiation" as defined herein refers to a method of exposing blood, either in vivo or ex vivo, to electromagnetic radiation for therapeutic purposes.

"Photopheresis" or "extracorporeal photopheresis" as defined herein refers to a method of treating blood by removing the blood from the body, exposing the blood to electromagnetic radiation, and reintroducing the blood into the body.

"MRSA" stands for methicillin-resistant *Staphylococcus aureus*. MRSA is a "staph" germ that results from contact of the skin with a surface containing the MRSA germ.

It is to be understood that both the foregoing general description and the following detailed description are exemplary and explanatory only and are not restrictive of the invention, as claimed. Reference will now be made in detail to exemplary embodiments of the present invention.

Phosphors are usually made from a suitable host material, to which an activator is added. Suitable activators that may be used in the present invention include ytterbium, erbium, thulium, holmium, and combinations of these materials. Non-limiting examples of activator couples include ytterbium/erbium, ytterbium/thulium, and ytterbium/holmium.

Generally, host materials comprise oxides, halides, sulfides, and selenides of various rare earth metals. Suitable phosphor host materials that may be used in one embodiment of the present invention include gadolinium, yttrium, lanthanum, and combinations of these materials. Particular non-limiting embodiments of such crystal matrices which may comprise the host material include oxy-sulfides, oxy-fluorides, oxychlorides, or vanadates of various rare earth metals.

Non-limiting embodiments of the organic and/or inorganic phosphors that can be used as host materials in the present disclosure include sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3Tb$), gadolinium oxysulphide:europium ($Gd_2O_2S$:Eu); lanthanam oxysulphide:europium ($La_2O_2S$:Eu); and gadolinium oxysulphide:promethium, cerium, fluorine ($Gd_2O_2S$:Pr,Ce,F); and generally (YLuScA)$PO_4$, wherein A is an activator selected from the group of bismuth, praseodymium and neodymium.

Other phosphors which may be used in the present composition, along with their characteristic absorption colors (and wavelengths) include, are not limited to: $Gd_2O_2S$:Tb (P43), green (peak at 545 nm); $Gd_2O_2S$:Eu, red (627 nm); $Gd_2O_2S$:Pr, green (513 nm); $Gd_2O_2S$:Pr,Ce,F, green (513 nm); $Y_2O_2S$:Tb (P45), white (545 nm); $Y_2O_2S$:Tb red (627 nm); $Y_2O_2S$:Tb, white (513 nm); Zn(0.5)Cd(0.4)S:Ag green (560 nm); Zn(0.4)Cd(0.6)S:Ag (HSr), red (630 nm); $CdWO_4$, blue (475 nm); $CaWO_4$, blue (410 nm); $MgWO_4$, white (500 nm); $Y_2SiO_5$:Ce (P47), blue (400 nm); $YAlO_3$:Ce (YAP), blue (370 nm); $Y_3Al_5O_{12}$:Ce (YAG), green (550 nm); $Y_3(Al,Ga)_5O_{12}$:Ce (YGG), green (530 nm); CdS:In, green (525 nm); ZnO:Ga, blue (390 nm); ZnO:Zn (P15), blue (495 nm); (Zn,Cd)S:Cu,Al (P22G), green (565 nm); ZnS:Cu,Al, Au (P22G), green (540 nm); ZnCdS:Ag,Cu (P20), green (530 nm); ZnS:Ag (P11), blue (455 nm); $Zn_2SiO_4$:Mn (P1), green (530 nm); ZnS:Cu (GS), green (520 nm); and the following crystals that emit in a UV-C range, e.g., from 200 to 280 nm, such as from 225 to 275 nm: $YPO_4$:Nd; $LaPO_4$:Pr; (Ca,Mg)$SO_4$:Pb; $YBO_3$:Pr; $Y_2SiO_5$:Pr; $Y_2Si_2O_7$:Pr; $SrLi_2SiO_4$:Pr,Na; and $CaLi_2SiO_4$:Pr.

In one embodiment, the organic and/or inorganic phosphors are present in the disclosed composition in an amount effective to convert electromagnetic radiation of a frequency (A) to a higher frequency (B). While in theory, the up-converting crystals of this embodiment can convert any electromagnetic energy to a higher energy (or shorter wavelength), in one embodiment, the electromagnetic radiation of frequency (A) comprises infrared or visible light, and the frequency (B) comprises ultraviolet (UV) radiation chosen from UVA, UVB, and UVC.

The organic and/or inorganic phosphors may be present in the disclosed composition in an amount ranging from 0.01% to 60% by weight, relative to the total weight of the composition, such as from 0.1% to 30% or even 1% to 15% by weight, relative to the total weight of the composition.

In one embodiment, the disclosed composition may further comprise an activator for the organic and/or inorganic phosphors, such as a ytterbium containing activator. Non-limiting examples of the ytterbium containing activator include ytterbium/erbium, ytterbium/thulium, ytterbium/terbium, and ytterbium/holmium.

The organic and/or inorganic phosphors according to the present disclosure typically have an average particle size ranging from 1 nm to 1 cm, such as from 1 nm to 1 mm, from 2 nm to 1000 nm, from 5-100 nm, or even 10-50 nm. The concentration of the organic and/or inorganic phosphors in the inventive composition as well as in the above-defined regions and the size of the organic and/or inorganic phosphors can be measured by methods known for such which are well known in the art. For example, x-ray diffraction (XRD), scanning electron microscopy (SEM), transmission electron microscopy (TEM), and/or BET surface area analysis may be used.

The organic and/or inorganic phosphors according to the present disclosure are typically synthesized from rare-earth doped phosphorescent oxide particles having the previously described sizes. The method further provides for homogeneous ion distribution through high temperature atomic diffusion.

A solid-phase precursor composition (hereinafter referred to as "the precursor composition") is prepared by mixing one or more rare earth element dopant precursor powders with one or more oxide-forming host metal powders. Stoichiometric amounts of host metal and rare earth element are employed to provide rare earth element doping concentrations in the final particle of at least 0.5 mol % up to the quenching limit concentration.

In one embodiment, the quenching limit concentration is about 15-18 mol % for europium-doped $Y_2O_3$ nanoparticles, while it is about 10 mol % for erbium-doped $Y_2O_3$ nanoparticles. Also, for Yb and Er-codoped $Y_2O_3$ nanoparticles, the quenching limit depends upon the ratio of Yb:Er.

The rare earth element dopant precursor powders include, but are not limited to organometallic rare earth complexes having the structure:

$$RE(X)_3$$

wherein X is a trifunctional ligand and RE is a rare earth element. Any rare earth element or combinations thereof can be used (i.e., europium, cerium, terbium, dysprosium, holmium, erbium, thulium, ytterbium, lutetium) with particular mention being made to europium, cerium, terbium, holmium, erbium, thulium and ytterbium, as well as the following combinations: ytterbium and erbium, ytterbium and holmium and ytterbium and thulium.

Strontium can also be used, and for purposes of the present invention, rare earth elements are defined as including strontium are earth element dopant precursor powders include $Yb(TMHD)_3$, $Er(TMHD)_3$, $Ho(TMHD)_3$, $Tm(TMHD)_3$, erbium isopropoxide ($C_9H_{21}O_3Er$), ytterbium isopropoxide ($C_9H_{21}O_3Yb$), and holmium isopropoxide ($C_9H_{21}O_3Ho$).

Examples of trifunctional ligands include tetramethylheptanedionate (TMHD), isopropoxide (IP), and the like.

The oxide forming host metal can be, but is not limited to, lanthanum, yttrium, lead, zinc, cadmium, and any of the Group II metals such as, beryllium, magnesium, calcium, strontium, barium, aluminum, radium and any mixtures thereof or a metalloid selected from silicon, germanium and II-IV semi-conductor compounds. Oxide-forming host metal powders include $Y(TMHD)_3$, $Al(TMHD)_3$, $Zr(TMHD)_3$, Y(IP), and Ti(IP).

The rare earth element dopant precursor powder and oxide-forming host metal powders are mixed to form the precursor composition, and vaporized. An inert carrier gas, such as, but not limited to, nitrogen, argon, helium, and mixtures thereof, transports the vaporized precursor composition to a low pressure combustion chamber that houses a flame.

The flame produces active atomic oxygen via chain-initiation reaction of $$H+O_2=OH+O \qquad (i)$$

A high concentration of oxygen in the flame activates and accelerates the oxidation of rare-earth ions and host materials through a series of reactions:

$$R+O \rightarrow RO; \qquad (ii)$$

$$RO+O \rightarrow ORO; \text{ and} \qquad (iii)$$

$$ORO+RO \rightarrow R_2O_3 \qquad (iv)$$

Reactions (ii) through (iv) are much faster than the oxidation reaction in low temperature processing represented by the reaction below;

$$2R+3/2O_2=R_2O_3 \qquad (v)$$

The reaction represented by formula (v) has a much higher energy barrier than the reactions in formulae (i)-(iv) in which radicals formed in flames diffuse and help produce faster ion incorporation.

Generally, in flame spray pyrolysis a higher flame temperature increases particle sintering and agglomeration. However, in one embodiment of the present invention, spherical, discrete particles are formed. It is proposed that in addition to residence time, the initial size of the vapor-phase particles in the vaporized precursor composition and the precursor itself are the dominant factors that determine final particle size. As the vaporized precursor composition passes through the flame, it directly reacts and releases heat to the flame increasing flame temperature. Thus, a shorter flame residence time is needed, which allows for the production of smaller particles.

Temperatures ranging from about 1800 to about 2900° C. are used in one embodiment, with temperatures ranging from about 2200 to about 2400° C. being particularly noted. Temperatures within this range produce monodispersed rare earth doped activated oxide nanoparticles without significant agglomeration having an essentially uniform distribution of rare earth ions within the particles. Actual residence time will depend upon reactor configuration and volume, as well as the volume per unit time of vaporized precursor composition delivered at a given flame temperature. Cubic phase particles are obtained having an average particle size ranging from 5 to 50 nanometers, such as from 10 to 20 nanometers. Until recently, it was not possible to obtain activated cubic phase particles on a nanoscale. The particles also exhibit quenching limit concentrations heretofore unobtained.

The flame temperature can be manipulated by adjusting the flow rates of the gas(es). For example, the temperature of the flame can be increased by increasing the methane flow rate in a methane/oxygen gas mixture. Guided by the present specification, one of ordinary skill in the art will understand without undue experimentation how to adjust the respective flow rates of reactive gas(es) and inert carrier gas to achieve the flame temperature producing the residence time required to obtain an activated particle with a predetermined particle size.

Any reactive gas can be used singularly or in combination to generate the flame for reacting with the vaporized precursor composition, such as, but not limited to, hydrogen, methane, ethane, propane, ethylene, acetylene, propylene, butylenes, nbutane, iso-butane, n-butene, iso-butene, n-pentane, iso-pentane, propene, carbon monoxide, other hydrocarbon fuels, hydrogen sulfide, sulfur dioxide, ammonia, and the like, and mixtures thereof.

A hydrogen flame can produce high purity nano-phosphors without hydrocarbon and other material contamination. In the depicted embodiments, the flame length determines particle residence time within the flame. Higher temperatures produce satisfactory nanoparticles with shorter flames. Flame length is similarly manipulated by varying gas flow rates, which is also well understood by the ordinarily skilled artisan. Increasing the flame length increases the residence time of the particles in the flame allowing more time for the particles to grow. The particle residence time can be controlled by varying the different flow rates of the gases, and is readily understood by one of ordinary skill in the art guided by the present specification.

The compositions according to the invention further comprise at least one organic or inorganic media in or on which the disclosed phosphors are dispersed. In one embodiment, the organic media comprises a plastic resin, such as thermoplastic elastomers, high temperature plastics, and engineering thermoplastics. Non-limiting examples of such resins include a polymer or co-polymer of polyvinyl chloride (PVC), acrylonitrile butadiene styrene (ABS), olefin, polycarbonate, styrene, nylon, and acetal.

It is possible to obtain an intimate mixture of the described phosphors and resins by mixture them in a dry state and subsequently compounding them, which may be followed by forming them into desired shapes using known plastic forming techniques, such as injection molding.

The resins described herein are well-known to be formed into a variety of plastic consumer and household goods, including hair combs, toothbrushes (and bristles), toilet seats, household surfaces, waste receptacles, waste receptacle liners, appliances, refrigerator surfaces, refrigerator interiors, as well as in all types of food packaging.

In addition to toothbrushes, there is disclosed other body brushes, such as shower brushes and face brushes in which the bristles comprise the disclosed phosphors. For example, by including the phosphors on a face brush, such as a Clarisonic® Brush, one could impart antimicrobial properties that were not otherwise present.

Food packaging made from the inventive composition makes it possible to reduce the occurrence of common food bacteria, such *E. coli* and *salmonella*, simply by exposing it to light, even while sitting on a store shelf. Thus, it may be possible to extend the life of a product by using packaging made from the disclosed composition.

In another embodiment, the media is inorganic and comprises a ceramic, metal or fabric. For example, the inorganic media may be ceramic and/or comprise glass or porcelain. In one embodiment, the end-use is for a kitchen or bathroom fixture. Non-limiting examples of such fixtures include shower heads, toilets, sinks, bathtubs, showers, countertops, wall materials, wall coverings, floor materials, floor coverings, ceiling materials, ceiling coverings, handles, knobs, tiles, appliances, refrigerator surfaces, waste receptacles, waste receptacle liners, and any household surfaces. Use of such compositions make it possible to form eating and cooking utensils that are resistant to common food bacteria, such *E. coli* and *salmonella*.

In one embodiment, the disclosed composition is used in a medical device. Non-limiting examples of such medical devices include intralumen devices, such as stents, guidewires, and embolic filters. Common materials that can be used in such intralumen devices include metals chosen from stainless steel or an alloy of nickel and titanium, commonly referred to as "NiTinols."

When coated on such devices, it would be possible to achieve localized UVC treatment even when such a device is inserted in the body. For example, by exposing the body to infrared (IR) radiation, which passes through the body, the IR radiation will convert to UVC radiation or radiation of a shorter wavelength such as x-rays or gamma rays when it comes into contact with coated devices. This localized treatment will inhibit abnormal cell growth within the body, commonly referred to as "restenosis", which remains a major limitation of percutaneous coronary intervention (PCI).

Other non-limiting examples of medical devices that may benefit from being coated with the inventive composition include needles, catheters, indwelling catheters such as intravenous catheters and urinary catheters, outdwelling catheters, surgical instruments, blood pressure cuffs, gloves, white coats, all types of scopes, material to be implanted into the body to repair or replace blood vessels, or to be implanted as mesh as in hernia repair, such as polytetrafluoroethylene or other fluoropolymer based materials, including those sold under the name Gortex®, valves for the heart or blood vessels, orthopedic devices such as prosthetic joints, ligaments, cartilage and the like, as well as neurosurgical implants, nerve stimulators, deep brain stimulators, and the like.

Another embodiment is directed to containers for collection and/or storage of bodily fluids and tissues, such as blood, blood components, serum, platelets, bone marrow, urine, and plasma. The plastic composition used in such containers typically includes a plastic resin that is suitable for contact with blood, such as polyvinyl chloride, polyolefin or polyester. Such containers must be able to withstand sterilization of the container, which is typically carried out at high temperatures.

It is possible, however, that exposure of such plastic compositions to high temperatures during steam sterilization, may cause degradation of the plastic composition. Degradation presents obvious problems, including a weakening of the overall mechanical strength of the container. To avoid this problem, it is possible to form a flexible sterilizable storage container for blood and blood components.

The plastic composition used in such containers typically includes a plastic resin that is suitable for contact with blood, such as polyvinyl chloride, polyolefin or polyester, which is compounded with the phosphors disclosed herein. In addition to sterilizing the blood storage vessel from the disclosed composition, the blood stored in the vessel and unwanted contaminants located therein, such as hepatitis, can be easily exposed to a lethal dose of radiation. Thus, in one embodiment, there is disclosed a method of treating blood products by exposing blood products that are contained in a vessel made of the composition disclosed herein, to an initial radiation, which when intersected with the disclosed composition, is converted to UVC radiation or electromagnetic radiation of shorter wavelengths, such as x-rays or gamma-rays.

There is also disclosed a chamber or cover, such as a glass or plastic piece, for containing or covering an article to be disinfected. In one embodiment, the article is placed within the chamber or cover for sterilization. For example, in one embodiment, there is disclosed a plastic piece for covering the head of a toothbrush or the diaphragm of a stethoscope. In this embodiment, the plastic cover is capable of emitting the longer wavelength radiation to activate the crystals and creating UV-C within the environment where the article is being disinfected. In one embodiment, the cover further comprises coating on at least one of the interior or exterior walls that blocks the UV-C from exiting the plastic cover, thus preventing UVC from reaching those in the environment outside of the article that is being disinfected. In one embodiment, the coating for containing the UVC comprises a thin metal layer, or an oxide that is transparent or translucent to the initial energy A but that prevent UVC from exiting the cover, such as MgO, $TiO_2$, $SiO_2$ and $Al_2O_3$.

In one embodiment, the cover may be used on top of any product described herein, such as a consumer product or medical device, including but not limited to a toothbrush, comb, razor, stethoscope, or dental implant.

In one embodiment, there is disclosed a mouth-guard that can be used in various sports, such as football, hockey, boxing, and the like, comprising the disclosed phosphors. As used in this paragraph and throughout the disclosure in general, "comprising the disclosed phosphor" is intended to mean the device, here the mouth-guard, includes the disclosed phosphors in any capacity, such as on the surface or compounded in the resin prior to forming the mouth-guard. In another embodiment, the previously described cover can be used on top of the mouth-guard.

Other sporting equipment that could benefit from the inventive composition includes all types of headgear used for protection in combat sports, such as boxing and mixed martial arts. In addition, helmets and padding used for virtually any team sport, such football, hockey, baseball, softball, lacrosse and the like, could benefit from antimicrobial and sterilizing properties. Equipment that can be impregnated or coated with the inventive composition includes but is not limited to gloves for catching balls and pucks, pads for protecting the shoulder, arms, legs, groin and other body parts.

In another embodiment, the organic or inorganic media comprises a fabric derived from natural or synthetic fibers or blends of such fibers. Non-limiting examples of the natural fibers comprise cotton, wool, silk, and combinations thereof. Non-limiting examples of the synthetic fibers are chosen from polyesters, polyamides, acrylics, olefins, aramids, such as Kevlar®, polyurethanes, polyethers, such as glycolpolyethylene glycols, Spandex®, vinyl polymers and copolymers, and combinations thereof. The polyesters comprise polyethyleneterephthalate and polypropyleneterephthalate, and the polyamides comprise nylon.

The foregoing natural and synthetic fibers and fabrics made from such fabrics, or combinations of such fabrics, can be impregnated or coated with the inventive compositions, and then formed into a bandage, gauze, sutures or other article for wound treatment. Such a bandage would mitigate the possibility of infection by exposing the wound to germicidal UV treatment. Wound treatments containing up-converting crystals are especially useful for treating wounds in remote areas, for example in developing countries or in military applications.

In addition, such treated fibers and fabrics can be incorporated into various personal items, for example backpacks, tents, sleeping bags, camping gear, bedding, bandanas, handkerchiefs, hats, socks, clothing, shoe and boot liners, swimwear, and the like to protect against pests or bacterial and/or fungal growth.

Rooms, for example hospital rooms or institutional rooms, are sometimes sterilized by robots administering UVC radiation to the entire room. Inclusion of the disclosed composition on room features such as room sheets, curtains, drapes, room dividers, floors, walls, ceilings, furniture, light fixtures, either by coating or by integration with the material itself, would allow a robot to administer radiation in the safer infrared or visible wavelengths. In one embodiment, ambient light within the room is sufficient to activate the disclosed compound and sterilize the room when the room contains one or more room features including the disclosed composition.

Similarly, up-converting crystals may be incorporated into various building supplies to prevent mold and mildew. Non-limiting examples of such building supplies include caulk, drywall, flooring, decking, rugs, carpet, paint, roofing, gutters, exterior wall treatments, tiles, and the like.

In one embodiment, up-converting crystals described herein may be applied to surfaces that could harbor germs that lead to skin infections. Non-limiting examples of such surfaces include bedding, flooring or furniture of hospitals, long-term care facilities, nurseries, schools and public transportation. In one embodiment, the surface may include a floor mat, preferably but not exclusively at least one surface of a mat used in a gymnasium, including a wrestling mat, yoga mat, boxing ring floor, mixed martial arts ring, and the like. In such an application, an appropriate wavelength of energy can impinge the surface of the mat to theoretically provide a continuous sterilization of a floor that is may be exposed to unwanted contaminants, such as staph, including MRSA.

In another embodiment, the inventive composition may be dispersed on a liquid medium to form a sprayable slurry. This embodiment is particularly suited to retro-fit existing articles to make them germicidal. For example, it is possible to coat an existing article, such as a kitchen counter, by spraying, dipping, or painting onto the article, a composition described herein.

In this embodiment, the organic or inorganic media comprises a liquid for forming a sprayable slurry comprising: (a) at least one polyurethane; (b) at least one acrylic polymer or copolymer; and (c) at least one mineral or organic fillers, the composition optionally containing at least one crosslinking agent. In one embodiment, at least one of (a) to (c) is contained in an aqueous medium.

It is envisioned that consumer products made from or coated with the inventive composition can undergo almost continuous germicidal treatment just by nature of it being exposed to visible light, whether ambient or for artificial. In addition to the foregoing, other advantageous end-uses include, but are not limited to, any article that comes into contact with the general public, including door knobs, handrails, telephones, school desks, seat and arm cushions and headrests on public transportation vehicles.

Other areas that would benefit from the use of articles made from the invention include hospitals and doctor offices. For example, furniture, toys and other articles that have an increased exposure to virus, bacteria, yeast and fungi and can be almost continuously treated by simply exposing them to light.

In certain embodiments, hospital, medical and laboratory equipment are treated with or otherwise incorporate the up-converting crystals for sterilization. For example, tissue culture hoods may be sterilized with UV light from up-converting crystals rather than incorporating a direct UV light source.

It is also known that everyday, hand-held electronic equipment, such as cell phones, MP3 players, and remote controls of all kinds, including for televisions, often carry germs from there constant exposure to dirty hands, sometimes of multiple users. Thus, in another embodiment, there are disclosed cases for covering such electronic equipment, primarily cases for covering cell phones, MP3 players, and remote controls, that comprise the inventive up-converting phosphors.

In one embodiment, there are disclosed products that may be used in photodynamic therapy, such as photopheresis. In this embodiment, a composition as disclosed herein, e.g., one that comprises at least one phosphor capable of converting an initial electromagnetic radiation having a particular wavelength (A) to electromagnetic radiation having a shorter wavelength (B), is included in device or receptacle that comes into contact with blood.

The resins, polymers, ceramics, metals or fabrics described herein may be formed into any shape of any size suitable for use in photodynamic therapy or photopheresis. Non-limiting examples of suitable shapes include rigid containers, flexible containers, semi-flexible containers, pouches, bags, tubing, membranes, drapes, arrays, lenses, reflectors and implantable medical devices.

Other non-limiting examples of medical products or devices that may benefit from incorporating or being coated with the up-converting composition include catheters, such as intravenous catheters and urinary catheters; surgical instruments; probes; material to be implanted into the body to repair or replace blood vessels, or to be implanted as mesh as in hernia repair, such as polytetrafluoroethylene or other fluoropolymer based materials, including those sold under the name Gortex®; valves for the heart or blood vessels; orthopedic devices such as prosthetic joints, ligaments, cartilage and the like; implantable discs; as well as neurosurgical implants, nerve stimulators, deep brain stimulators, and the like.

Non-limiting examples of the photosensitive agents used in photodynamic therapy or photopheresis include porphyrins, chlorophylls, psoralens and/or dyes. In one embodiment, the photosensitive agent is chosen from aminolevulinic acid (ALA), silicon phthalocyanine Pc 4, m-tetrahydroxyphenyl-chlorin (mTHPC), momo-L-aspartyl chlorin e6 (NPe6), 8-methoxypsoralen and combinations thereof. In one exemplary embodiment, the photosensitive agent is 8-methoxypsoralen, which is activated by UVA radiation having a wavelength between about 315 nm and about 400 nm.

In certain embodiments, the photosensitive agent is added to the sample prior to exposure to radiation. In the case of photopheresis, the photosensitive agent such as psoralen is added to the sample enriched in white blood cells prior to exposure to UV radiation from the up-converting composition.

In other embodiments, the photosensitive agent is introduced into the body for in vivo photodynamic therapy. The photosensitive agent may be introduced locally or systemically. If introduced systemically, the photosensitive agent may accumulate or be induced to accumulate in the targeted area.

In another embodiment, the method may be used to inhibit pathogens or abnormal cell growth within the body. This is typically used when the up-converting composition is in or on an implantable medical device, for example an implant, prosthetic, probe or implantable disc. Radiation having wavelength (A), for example infrared light, which can penetrate skin and tissue, is directed at the part of the body in which the device is implanted. The up-converting composition converts the infrared light to UV light to target particular areas or cells within the body, for example pathogens or diseased, malignant or abnormal cells. In one embodiment, this localized treatment will inhibit abnormal cell growth within the body, commonly referred to as "restenosis", which remains a major limitation of percutaneous coronary intervention ("PCI").

In another embodiment of the method used to inhibit pathogens or abnormal cell growth within the body, a photosensitive agent is first introduced to the area to be treated, and the converted UV light activates the photosensitive agent to target pathogens or abnormal cells within the body. The radiation having wavelength (A) may be directed at the particular area to be treated, or may be directed at a larger portion of the body or even the entire body. The radiation having wavelength (B) may be directed at the particular area to be treated or a larger portion of the body.

Another embodiment is directed to containers for collection, storage, and/or treatment of bodily fluids or tissues, such as blood, blood components and bone marrow. Treatment of the bodily fluids or tissues may include, for example, sterilizing the sample; or removing, activating or inactivating particular compounds, agents or cells in the sample. The plastic composition used in such containers typically includes a plastic resin that is suitable for contact with samples of bodily fluids or tissues.

Other household products that would benefit from the disclosed sterilization techniques include children's items including toys, cribs, bassinets, changing table pads, diapers, diaper pails, diaper pail liners, trash cans, trash bags, and the like.

In one embodiment, the up-converting crystals are incorporated into various military equipment to prevent or inhibit microbial growth, as well as protect against bioterrorism. Non-limiting examples of such equipment includes firearms, clothing, protective gear, backpacks, bedding, upholstery, tents, and the like.

Another embodiment is directed to containers for collection, storage, and/or treatment of fluids. For example, gasoline and other hydrocarbons such as brake fluid, coolants, reactor coolants, engine coolants, oils, lubricants and the like may be degraded by bacteria. In one embodiment, storage and/or treatment of such fluids in a container comprising the disclosed up-converting crystals and subsequent exposure of the up-converting crystals to visible and/or IR radiation results in any existing bacteria or other microbes being eliminated or inhibited by the resulting UV or shorter wavelength radiation, thus preventing or impeding microbial degradation.

In one embodiment, a container comprising the disclosed up-converting crystals is used to collect, store and/or treat fluids such as water or other beverages. Exposure of the up-converting crystals to the appropriate incident radiation and subsequent emission of UV or shorter wavelength radiation by the crystals can sterilize and/or inhibit the growth of pathogens and microbes within the contained fluid.

There is also disclosed a method of sterilizing an article by exposing it to UVC radiation or radiation of a shorter wavelength, the method comprising: exposing to long-wave ultraviolet, visible or infrared light, a composition comprising, in an organic or inorganic media, at least one phosphor capable of converting said visible or infrared light to UV radiation or radiation of a shorter wavelength, such as x-ray or gamma rays. In this embodiment, exposing is performed for a time sufficient to deactivate or kill at least one microorganism, including those chosen from bacteria, virus, mold, protozoa, and yeast.

In another embodiment, the method may be used to inhibit abnormal cell growth within the body. This is typically used when the composition is in or on an implantable medical device, such as a stent.

There is also disclosed a film comprising the disclosed up-converting phosphors wherein the film is applied to any surface, including the surfaces of the previously described articles, which will allow the articles to be "retro-fitted" to obtain sterilizing or antimicrobial properties.

In such an embodiment, the disclosed up-converting phosphors can be incorporated into a polymeric composition to form a film with significantly improved antimicrobial activity of agent(s) in the compositions. Films have been known to include antimicrobial promoters, including blowing agents and/or hydrophilic wetting agents which are added to a polymeric composition containing an antimicrobial agent. U.S. Published Application 2013/0025764, which is herein incorporated by reference in its entirety, describes polymeric films containing traditional antimicrobial agents. The polymeric composition can be coextruded to form a polymeric film. The film or layer can be incorporated into a wide range of articles and preferably used in a multilayer barrier assembly. Traditionally, the polymeric layer to which the antimicrobial promoter is added, includes at least one antimicrobial agent such as silver ion, zinc oxide, triclosan, and/or other antimicrobial agents. Unlike the prior art, the present invention includes polymeric layers having up-converting phosphors instead of, or in addition to traditional antimicrobial agents.

In one embodiment, films comprising the disclosed phosphors can have an adhesive backing that allows the film to be placed on any surface thereby providing antimicrobial and sterilizing properties. Non-limiting examples of such uses include temporary or long-term antimicrobial and sterilizing properties for articles not otherwise having such properties. By using such films, the films allows point-of-use sterilization for almost any article regardless of shape, size, age or material.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and in the attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

What is claimed is:

1. An article comprising a composition for converting electromagnetic radiation having wavelength (A) to electromagnetic radiation having a shorter wavelength (B), said composition comprising:
   at least one phosphor capable of converting an initial electromagnetic radiation having wavelength (A) to a different electromagnetic radiation having wavelength (B), said different electromagnetic radiation having wavelength (B) comprising UV, X-ray, or gamma radiation; and
   an organic or inorganic media containing said phosphor,
   said article comprising a consumer product, a children's toy, an animal toy, a medical device, medical product, a receptacle for fluids, a receptacle for holding drinking water, a bathroom fixture, a kitchen fixture, eating or cooking utensils, a cleaning product, an article of clothing, a building or construction article, sporting equipment, electronic equipment, or a polymeric film.

2. The article of claim 1, wherein said consumer product is chosen from a toothbrush, a comb, a hair brush, a shower mat, or a toilet seat.

3. The article of claim 1, wherein said consumer product is chosen from a children's product, an infant's product, a changing table pad, a diaper, a diaper pail, a piece of furniture, a crib, a bassinet, a trash can, a trash bag, camping equipment, a backpack, a tent, a sleeping bag, or bedding.

4. The article of claim 1, wherein said medical device is implantable in a human body and comprises a prosthetic device, a catheter, an intralumenal device chosen from a stent, guidewire, or embolic filter, a needle, an indwelling catheter, an intravenous catheter, a urinary catheter, an outdwelling catheter, surgical instruments, a blood pressure cuff, a glove, a white coat, a scope, material to be implanted into the body to repair or replace blood vessels, components to be implanted as mesh as in hernia repair, valves for the heart or blood vessels, orthopedic devices, neurosurgical implants, nerve stimulators, and deep brain stimulators.

5. The article of claim 1, wherein said is medical product comprises an article for covering a wound chosen from a bandage, a gauze, or a suture.

6. The article of claim 1, wherein said receptacle for fluids comprises a receptacle for biological fluids, blood, blood components, serum, platelets, bone marrow, urine, plasma, medical fluids, beverages, drinking water, water, household fluids, industrial fluids, automotive fluids, gasoline, fluid hydrocarbons, brake fluid, coolants, reactor coolants, engine coolants, oils, lubricants.

7. The article of claim 1, wherein said bathroom fixture comprises a bathroom surface, a shower head, a toilet, a toilet seat, a sink, a bathtub, a shower, a countertop, a wall material, a wall covering, a floor material, a floor covering, a ceiling material, a ceiling covering, a waste receptacle, a waste receptacle liner, a handle, a knob, or a tile.

8. The article of claim 1, wherein said kitchen fixture comprises a kitchen surface, a sink, an appliance, a refrigerator surface, a refrigerator interior surface, a waste receptacle, a waste receptacle liner, a countertop, a wall material, a wall covering, a floor material, a floor covering, a ceiling material, a ceiling covering, a handle, a knob, or a tile.

9. The article of claim 1, wherein said polymeric film contains an adhesive on at least one surface.

10. The article of claim 1, wherein said cleaning product comprises a receptacle configured to contain an object to be sterilized.

11. The article of claim 1, wherein said article of clothing comprises clothing, socks, a clothing accessory, a bandana, a handkerchief, a hat, a shoe liner, a boot liner, or swimwear.

12. The article of claim 1, wherein said building or construction article comprises, caulk, drywall, flooring, decking, rugs, carpet, paint, roofing, a gutter, an exterior wall treatment, a tile, a room feature, a room sheet, a curtain, a drape, a room divider, a floor material, a floor covering, a wall material, a wall covering, a ceiling material, a ceiling covering, a piece of furniture, or a light fixture.

13. The article of claim 1, said article comprising a piece of hospital equipment, a piece of medical equipment, a piece of laboratory equipment, or a tissue culture hood.

14. The article of claim 1, wherein said sporting equipment comprises a mouth-guard, headgear for protection against combat sports, a helmet, gloves for catching balls and pucks, pads for protecting the body, and floor mats.

15. An article comprising the composition of claim 1, said article comprising a cover for a medical device or consumer product that:
   is transparent or translucent to said initial electromagnetic radiation having wavelength (A) and converts said initial energy to electromagnetic radiation having a shorter wavelength (B).

16. The article of claim 15, wherein said cover further comprises a coating on at least one surface that is transparent or translucent to the initial energy but that prevents UV from exiting the cover.

17. The article of claim 16, wherein said at least one coating comprises a metal or oxide chosen from MgO, $TiO_2$, $SiO_2$ and $Al_2O_3$.

18. The article of claim 16, wherein said consumer product and medical device is chosen from a toothbrush, comb, razor, body or face brush, stethoscope, and dental implant.

19. The article of claim 1, wherein the initial electromagnetic radiation having wavelength (A) comprises infrared radiation or visible light.

20. The article of claim 1, wherein said at least one phosphor has an average particle size ranging from 1 nm to 1 cm.

21. The article of claim 1, wherein said at least one phosphor is present in an amount ranging from 0.01% to 60% by weight, relative to the total weight of the composition.

22. The article of claim 1, wherein said organic media comprises a plastic resin, comprising a polymer or co-polymer of polyvinyl chloride (PVC), acrylonitrile butadiene styrene (ABS), olefin, polycarbonate, styrene, nylon, and acetal.

23. The article of claim 1, wherein said inorganic media comprises a ceramic, metal or fabric.

24. The article of claim 1, wherein said ceramic comprises glass or porcelain, and said metal comprises stainless steel or an alloy of nickel and titanium.

25. The article of claim 1, wherein said fabric is derived from natural or synthetic fibers or blends of such fibers, wherein said natural fibers comprise cotton, wool, silk, and combinations thereof, and said synthetic fibers are chosen from polyesters, polyamides, acrylics, olefins, aramids, fluropolymers, polyurethane, polyethers, vinyl polymers and copolymers, and combinations thereof.

26. The article of claim 1, wherein said organic or inorganic media comprises a liquid for forming a sprayable slurry of said composition.

27. The article of claim 26, wherein said liquid comprises:
(a) at least one polyurethane;
(b) at least one acrylic polymer or copolymer; and
(c) at least one mineral or organic fillers;
said composition optionally containing at least one crosslinking agent.

28. The composition of claim 27, wherein at least one of (a) to (c) is contained in an aqueous medium.

29. A method of sterilizing an article by exposing it to UV radiation or radiation of a shorter wavelength, said method comprising:
exposing to long-wave ultraviolet, visible or infrared light, a composition comprising, in an organic or inorganic media, at least one phosphor capable of converting said visible or infrared light to UV radiation or radiation of a shorter wavelength,
wherein said exposing is performed for a time sufficient to deactivate or kill at least one microorganism chosen from bacteria, virus, mold, protozoa, and yeast;
and/or for a time sufficient to inhibit abnormal cell growth within the body, when said composition is in an implantable medical device.

30. The method of claim 29, wherein said bacteria is chosen from: *E. coli, salmonella, staphylococcus, streptococcus, legionella, bacillus, rhodospirillum, mycobacterium, clostridium*, dysentery, and tuberculosis.

31. The method of claim 29, wherein said virus is chosen from bacteriophage, coxsackie, infectious hepatitis, influenza, and rotavirus.

32. The method of claim 29, wherein said at least phosphor comprises an activator comprising ytterbium, bismuth, praseodymium and neodymium.

33. The method of claim 29, wherein the initial electromagnetic radiation of frequency (A) comprises infrared radiation or visible light.

34. The method of claim 29, wherein said at least one phosphor is present in an amount ranging from 0.01% to 60% by weight, relative to the total weight of the composition.

35. The method of claim 29, wherein said radiation of a shorter wavelength comprises X-ray or gamma radiation.

* * * * *